(12) United States Patent
Asaumi et al.

(10) Patent No.: US 8,237,002 B2
(45) Date of Patent: Aug. 7, 2012

(54) METHOD FOR PRODUCING UNSATURATED ORGANIC COMPOUND

(75) Inventors: Taku Asaumi, Kobe (JP); Takashi Kamikawa, Nara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 96 days.

(21) Appl. No.: 12/989,900

(22) PCT Filed: Apr. 28, 2009

(86) PCT No.: PCT/JP2009/058726
§ 371 (c)(1), (2), (4) Date: Oct. 27, 2010

(87) PCT Pub. No.: WO2009/136646
PCT Pub. Date: Nov. 12, 2009

(65) Prior Publication Data
US 2011/0046380 A1 Feb. 24, 2011

(30) Foreign Application Priority Data

May 8, 2008 (JP) ................ 2008-122021

(51) Int. Cl.
*C07C 1/00* (2006.01)
*C07C 1/20* (2006.01)
(52) U.S. Cl. .............. 585/469; 585/446; 585/457
(58) Field of Classification Search ............ 585/469, 585/446, 457
See application file for complete search history.

(56) References Cited

U.S. PATENT DOCUMENTS
2006/0224011 A1  10/2006  Ishikawa et al.

FOREIGN PATENT DOCUMENTS

| JP | 2004-091467 A | 3/2004 |
|---|---|---|
| JP | 2004-189599 A | 7/2004 |
| JP | 2005-008578 A | 1/2005 |
| JP | 2006-306758 A | 11/2006 |

OTHER PUBLICATIONS

Galland et al., "Cross-Coupling of Chloroarenes with Boronic Acids using a Water-Soluble Nickel Catalyst", Tetrahedron Letters, vol. 40, pp. 2323-2326, (1999).
Int'l Search Report issued on Aug. 4, 2009 in Int'l Application No. PCT/JP2009/058726.
Int'l Preliminary Report on Patentability issed on Dec. 13, 2010 in Int'l Application No. PCT/JP2009/058726.

*Primary Examiner* — Thuan Dinh Dang
(74) *Attorney, Agent, or Firm* — Panitch Schwarze Belisario & Nadel LLP

(57) ABSTRACT

A method for producing an unsaturated organic compound represented by the formula (3):

$$(Y^1)_{m-1}—R^1—R^2—(Y^2)_{n-1} \qquad (3)$$

wherein $Y^1$ represents $R^2$ or $X^1$, and $Y^2$ represents $R^1$ or $B(X^2)_2$, which comprises reacting a compound represented by the formula (1):

$$R^1(X^1)_m \qquad (1)$$

wherein $R^1$ represents an aromatic group or the like, $X^1$ represents a leaving group and m represents 1 or 2, with a compound represented by the formula (2):

$$R^2\{B(X^2)_2\}_n \qquad (2)$$

wherein $R^2$ represents an aromatic group or the like, $X^2$ represents a hydroxyl group or the like, and n represents 1 or 2, in the presence of
(a) a nickel compound selected from a nickel carboxylate, nickel nitrate and a nickel halide,
(b) a phosphine compound such as 1,4-bis(dicyclohexylphosphino) butane,
(c) an amine selected from a primary amine and a diamine such as N,N,N',N'-tetramethyl-1,2-ethanediamine, and
(d) an inorganic base.

9 Claims, No Drawings

METHOD FOR PRODUCING UNSATURATED ORGANIC COMPOUND

CROSS-REFERENCE TO RELATED APPLICATION

This application is a section 371 of International Application No. PCT/JP2009/058726, filed Apr. 28, 2009, which was published in the Japanese language on Nov. 12, 2009 under International Publication No. WO 2009/136646 A1 and the disclosure of which is incorporated herein by reference.

TECHNICAL FIELD

The present invention relates to a method for producing an unsaturated organic compound.

BACKGROUND ART

Unsaturated organic compounds are useful compounds as medicines, agrichemicals, liquid crystal materials, organic EL materials and synthetic intermediates thereof, and among them, the demand for compounds having a biaryl structure is increasing. As the method for producing an unsaturated organic compound having a biaryl structure, a method of coupling a aryl halide with a boron compound using a palladium catalyst or a nickel catalyst has been known. Especially, from the viewpoint that a nickel catalyst is cheaper, a development of a coupling reaction using a nickel catalyst is desired industrially.

For example, Tetrahedron Letters, 1999, 40, 2323-2326 discloses a coupling reaction of an arylboric acid and an aryl chloride using $NiCl_2(dppe)$ catalyst.

DISCLOSURE OF THE INVENTION

The present invention provides:
<1> A method for producing an unsaturated organic compound represented by the formula (3):

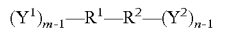  (3)

wherein $R^1$ represents a substituted or unsubstituted m-valent aromatic group, a substituted or unsubstituted m-valent heteroaromatic group, or a substituted or unsubstituted m-valent aliphatic hydrocarbon group having at least one double bond, $R^2$ represents a substituted or unsubstituted n-valent aromatic group, a substituted or unsubstituted n-valent heteroaromatic group, or a substituted or unsubstituted n-valent aliphatic hydrocarbon group having at least one double bond, m represents 1 or 2, n represents 1 or 2, with the proviso that when m is 2, n is 1, $Y^1$ represents $R^2$ or $X^1$, $Y^2$ represents $R^1$ or $B(X^2)_2$, $X^1$ independently represents a leaving group bonded to a $sp^2$ carbon, $X^2$ independently represents a hydroxyl group or an alkoxy group, or two $X^2$ are bonded to a ring containing a boron atom, and a group represented by $—B(X^2)_2$ are bonded to a $sp^2$ carbon, which comprises reacting a compound represented by the formula (1):

  (1)

wherein $R^1$, $X^1$ and m are the same as defined above, with a compound represented by the formula (2):

  (2)

wherein $R^2$, $X^2$ and n are the same as defined above, in the presence of
(a) at least one nickel compound selected from the group consisting of a nickel carboxylate, nickel nitrate and a nickel halide, (b) a phosphine compound represented by the formula (A):

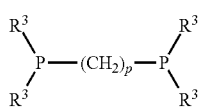  (A)

wherein $R^3$ is independently in each occurrence a C3-C7 alkyl group or a C3-C7 cycloalkyl group, and p represents 2, 3 or 4,
(c) at least one amine selected from the group consisting of a primary amine and an amine represented by the formula (B):

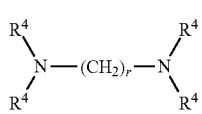  (B)

wherein $R^4$ is independently in each occurrence a substituted or unsubstituted C1-C10 alkyl group, and r represents an integer of 1 to 6, and
(d) an inorganic base;
<2> The method according to <1>, wherein the compound represented by the formula (1) is a compound represented by the formula (4):

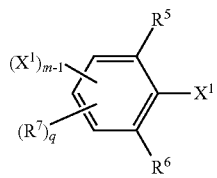  (4)

wherein $X^1$ and m are the same as defined above, $R^5$ and $R^6$ each independently represent a hydrogen atom, a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group,
$R^7$ is independently in each occurrence a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, q represents an integer of 0 to (4-m), and herein, $R^5$, $R^6$ or $R^7$ may be bonded with the neighboring substituent to form a ring together with the carbon atom to which it is bonded;

<3> The method according to <1> or <2>, wherein the compound represented by the formula (2) is a compound represented by the formula (5):

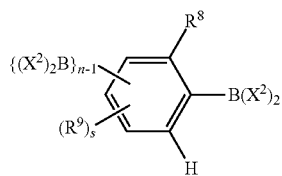

(5)

wherein $X^2$ and n are the same as defined above, $R^8$ represents a hydrogen atom, a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, $R^9$ represents a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, s represents an integer of 0 to (4-n), and herein, $R^8$ or $R^9$ may be bonded with the neighboring substituent to form a ring together with the carbon atom to which it is bonded;

<4> The method according to any one of <1> to <3>, wherein the nickel carboxylate is nickel acetate and the nickel halide is nickel chloride or nickel bromide;

<5> The method according to any one of <1> to <4>, wherein $R^3$ is a C3-C7 cycloalkyl group;

<6> The method according to <5>, wherein $R^3$ is a cyclohexyl group;

<7> The method according to any one of <1> to <6>, wherein p is 4;

<8> The method according to any one of <1> to <7>, wherein at least one amine selected from the group consisting of a primary amine and an amine represented by the formula (B) is an aliphatic primary amine.

BEST MODE FOR CARRYING OUT THE PRESENT INVENTION

In the formula of the compound represented by the formula (1):

$$R^1(X^1)_m \quad (1)$$

(hereinafter, simply referred to as the compound (1)), $R^1$ represents a substituted or unsubstituted m-valent aromatic group, a substituted or unsubstituted m-valent heteroaromatic group, or a substituted or unsubstituted m-valent aliphatic hydrocarbon group having at least one double bond, and $X^1$ independently represents a leaving group bonded to a $sp^2$ carbon, and m represents 1 or 2.

Examples of the m-valent aromatic group include a C6-C16 m-valent aromatic group having one to three aromatic rings. Specific examples thereof include a monovalent aromatic group such as a phenyl group, a naphthyl group, an anthryl group, a phenanthryl group, an indenyl group and a fluorenyl group, and a divalent aromatic group such as a phenylene group, a naphthalenediyl group, an anthracenediyl group, a phenanthrendiyl group, an indenediyl group and a fluorenediyl group.

The m-valent aromatic group may have a substituent, and examples thereof include a fluorine atom; a C1-C10 alkyl group which may have a fluorine atom such as a methyl group, an ethyl group, an n-propyl group, an isopropyl group, an n-butyl group and a trifluoromethyl group; a C3-C10 cycloalkyl group such as a cyclohexyl group; a hydroxyl group; a C1-C20 alkoxy group such as a methoxy group, an ethoxy group and a tert-butoxy group; a substituted or unsubstituted C6-C20 aryl group such as a phenyl group; a substituted or unsubstituted C6-C20 aryloxy group such as a phenoxy group; a substituted or unsubstituted C6-C20 arylthio group such as a phenylthio group; a cyano group; a substituted or unsubstituted amino group; a substituted or unsubstituted aminocarboxy group; a C1-C10 alkylsulfonylamino group such as a methylsulfonylamino group; a C6-C20 arylsulfonylamino group such as a phenylsulfonylamino group; a C2-C10 alkyl group having an N-substituted imino group at 1-position such as a 1-(N-methylimino)-1-ethyl group and a 1-(N-phenylimino)-1-ethyl group; a C7-C20 aralkyl group having an N-substituted imino group such as a 1-(N-methylimino)-1-phenylmethyl group and a 1-(N-phenylimino)-1-phenylmethyl group; an imido group such as a phthalimido group, a C1-C20 aliphatic or aromatic acyl group such as a formyl group, an acetyl group and a benzoyl group; a carboxyl group; a C2-C20 alkoxycarbonyl group such as a methoxycarbonyl group; a C7-C10 aryloxycarbonyl group such as a phenoxycarbonyl group; a substituted or unsubstituted aminosulfonyl group or a substituted or unsubstituted carbamoyl group; and a substituted or unsubstituted five- to seven-membered heteroaryl group containing one to three heteroatoms selected from the group consisting of a nitrogen atom, an oxygen atom and a sulfur atom such as a pyridyl group, a quinazolyl group, a pyrimidyl group, a furyl group, a thienyl group, a pyrrolyl group and an imidazolyl group.

Examples of the substituents of the substituted aryl group, the substituted aryloxy group, the substituted arylthio group and the substituted heteroaryl group include the same as those of the above-mentioned m-valent aromatic group.

Examples of the substituted amino group include an amino group substituted with a C1-C10 alkyl group such as a dimethylamino group and a diethylamino group, an amino group substituted with a C3-C10 cycloalkyl group such as a cyclohexylamino group, an amino group substituted with a C6-C20 aryl group such as a phenylamino group and a diphenylamino group, an amino group substituted with a C2-C10 alkoxycarbonyl group such as a methoxycarbonylamino group and a tert-butoxycarbonylamino group, an amino group substituted with a C6-C20 aryloxycarbonyl group such as a phenoxycarbonylamino group, and a morpholino group.

Examples of the substituted aminocarboxy group include an aminocarboxy group substituted with a C1-C10 alkyl group or a C6-C20 aryl group such as an N,N-dimethylaminocarboxy group, an N-methylaminocarboxy group, an N-tert-butylaminocarboxy group and an N-phenylaminocarboxy group.

Examples of the N-substituted imino group include an imino group substituted with a C1-C10 alkyl group such as N-methylimino group, and an imino group substituted with a C6-C20 aryl group such as N-phenylimino group.

Examples of the substituted aminosulfonyl group include an aminosulfonyl group substituted with a C1-C10 alkyl group such as an N-methylaminosulfonyl group and an N,N-dimethylaminosulfonyl group, and an aminosulfonyl group substituted with a C6-C20 aryl group such as an N-phenylaminosulfonyl group.

Examples of the substituted carbamoyl group include a carbamoyl group substituted with a C1-C10 alkyl group such as an N-methylcarbamoyl group and an N, N-dimethylcarbamoyl group, and an aminocarbamoyl group substituted with a C6-C20 aryl group such as an N-phenylcarbamoyl group.

These substituents may be bonded to the neighboring substituent to a ring together with the carbon atom to which they are bonded.

Examples of the m-valent heteroaromatic group include a five- to seven-membered heteroaromatic group containing one to three heteroatoms selected from the group consisting of a nitrogen atom, an oxygen atom and a sulfur atom. Specific examples thereof include a monovalent heteroaromatic group such as a pyridyl group, a furyl group, a thienyl group, a pyrrolyl group, an imidazolyl group, a benzoxazolyl group and a benzothienyl group, and a divalent heteroaromatic group such as a pyridinediyl group, a furandiyl group, a thiophenediyl group, a pyrrolediyl group, an imidazolediyl group and a benzoxazolediyl group. The m-valent heteroaromatic group may also have a substituent and examples of the substituent include the same as those of the above-mentioned m-valent aromatic group.

Examples of the m-valent aliphatic hydrocarbon group having at least one double bond include a C2-C10 alkenyl group such as a vinyl group and a 1-propenyl group, a C5-C8 cycloalkenyl group such as a cyclohexenyl group and a cyclopentenyl group, a C2-C10 alkenediyl group such as an ethylenediyl group, a C4-C10 alkadienyl group such as a butadienediyl group, and a C5-C8 cycloalkadienyl group such as a cyclohexadienyl group. The m-valent aliphatic hydrocarbon group may also have a substituent and examples of the substituent include an oxo group and the same as those of the m-valent aromatic group. Specific examples of the aliphatic hydrocarbon group having the substituent include a 1,4-benzoquinon-2-yl group, a 6-oxo-1-cyclohexen-1-yl group, a 5-oxo-1-cyclopenten-1-yl group and a 2-phenylvinyl group.

Examples of the leaving group include a chlorine atom, a bromine atom, an iodine atom, a C1-C6 alkylsulfonyloxy group such as a methanesulfonyloxy group, a C1-C6 flourine-substituted alkylsulfonyloxy group such as a trifluoromethanesulfonyloxy group, a C6-C10 arylsulfonyloxy group such as a p-toluenesulfonyloxy group, and —N≡N$^+$. The leaving group is bonded to a sp$^2$ carbon of the m-valent aromatic group, the m-valent heteroaromatic group or the m-valent aliphatic hydrocarbon group. When the leaving group is —N≡N$^+$, the compound (1) usually has a counter anion such as a tetrafluoroborate anion.

Examples of the compound (1) include phenyl bromide, o-tolyl bromide, 4-tert-butylphenyl bromide, 2,6-dimethylphenyl bromide, 3,5-dimethylphenyl bromide, 2-(2-hydroxyethyl)phenyl bromide, 4-cyclohexylphenyl bromide, 3-bromobenzotrifluoride, β-bromostyrene, 3-bromo-4-chlorobenzotrifluoride, 2-naphthyl bromide, 9-bromoanthracene, 9,10-dibromoanthracene, 1,3-dibromobenzene, m-methoxyphenyl bromide, 4-bromobenzaldehyde, 1,4-dibromo-2-fluorobenzene, methyl 2-bromophenylacetate, methyl 3-bromophenylacetate, ethyl 4-bromophenylacetate, methyl 3-bromocinnamate, methyl 5-bromosalicylate, 4-bromobenzamide, 4-bromobenzonitrile, 9-bromophenanthrene, 2-bromofluorene, 5-bromoindanone, 2,7-dibromofluorene, 6-bromo-2-naphthol, 4,4'-dibromobiphenyl, 2-pyridyl bromide, 2-bromofuran, 3-bromofuran, 2-bromothiophene, 4-bromopyrazole, 2-bromothiazole, 2-methyl-5-bromobenzothiazole, 5-bromouracil, 8-bromoquinoline, 4-bromoisoquinoline, 1-benzyl-5-bromotetrazole, phenyl chloride, o-tolyl chloride, 4-tert-butylphenyl chloride, 3-chlorotoluene, 4-chlorotoluene, 2,6-dimethylphenyl chloride, 3,5-dimethylphenyl chloride, 4-cyclohexyl chloride, 2-chloroacetophenone, 4-chloroacetophenone, 2-chloro-4-fluorotoluene, methyl 2-chlorophenylacetate, methyl 3-chlorophenylacetate, ethyl 4-chlorophenylacetate, 3-chlorobenzophenone, 4-chloro-1-naphthol, 4-chloro-N,N-dimethylaniline, 4-chloro-N,N-diphenylaniline, 5-chloro-N,N-dimethylaniline, 5-chloro-2-methoxyaniline, methyl 2-chlorobenzoate, ethyl 4-chlorobenzoate, phenyl 2-chlorobenzoate, N-(2-chlorophenyl)acetamide, N-(4-chlorophenyl)acetamide, 2-chlorobenzyl cyanide, 1-naphthyl chloride, 2-naphthyl chloride, 9-chloroanthracene, 9,10-dichloroanthracene, 1,3-dichlorobenzene, 2-methoxyphenyl chloride, 3-methoxyphenyl chloride, 4-methoxyphenyl chloride, 3,5-dimethoxy-2-chlorotoluene, 3-chlorobenzonitrile, 2,7-dichloro-9-fluorenone, 2-chloro-3-morpholino-1,4-naphthoquinone, 3-chlorobenzaldehyde, 1,4-dichloro-2-fluorobenzene, 2-pyridyl chloride, 2-chloro-6-trifluoropyridine, 2-chloro-3-picoline, 1-(3-chlorophenyl)-3-methyl-2-pyrazolin-5-one, 3-chlorothiophene, 2-chloro-3-methylthiophene, 5-chloro-1-methylimidazole, 5-chloro-1-methylbenzotriazole, 5-chloro-1-phenyl-1H-tetrazole, 4-chloro-1-methylindole, 2-chlorobenzimidazole, 8-chloro-5-methoxyquinoline, 2-chlorobenzoxazole, 2-methyl-5-chlorobenzoxazole, 2-chlorobenzothiazole, 2-methyl-5-chlorobenzothiazole, 2,6-dichloropyridine, 3,5-dichloropyridine, 6-chloro-9-methyl-9H-purine, 2-chloropyrazine, 1,4-dichlorophthalazine, 2,4-dichloropyrimidine, phenyl iodide, o-tolyl iodide, 4-tert-butylphenyl iodide, 2,6-dimethylphenyl iodide, 3,5-dimethylphenyl iodide, 4-iodoacetophenone, ethyl 2-iodobenzoate, 2-naphthyl iodide, 9-iodoanthracene, 9,10-diiodoanthracene, 1,3-diiodobenzene, 3-methoxyphenyl iodide, N-tert-butoxycarbonyl-4-iodo-phenylalanine methyl ester, 4,4'- diiodobiphenyl, 2-methyl-5-iodobenzoxazole, 2-methyl-5-iodobenzothiazole, 1,4-diodo-2-fluorobenzene, 1-bromo-4-chlorobenzene, 4-chloroiodobenzene, 2-bromo-6-chlorotoluene, 2-pyridyl iodide, vinyl bromide, vinyl chloride, 1,2-ethylene dichloride, 1-bromo-1-cyclohexene, 1-chloro-1-cyclopentene, 2-methyl-5-(p-toluenesulfonyloxy)benzoxazole, 2,6-dimethylphenyl trifluoromethanesulfonate, 2-pyridyl trifluoromethanesulfonate, 2,2'-bis(trifluoromethanesulfonyloxy)-1,1'-binaphthalene, 1,2,2-trimethylvinyl trifluoromethanesulfonate, 1-trifluoromethanesulfonyloxy-1-cyclohexene, 2-methyl-5-(trifluoromethanesulfonyloxy)benzoxazole, 2-methyl-5-(trifluoromethanesulfonyloxy)benzothiazole, 4-bromophenyl trifluoromethanesulfonate, 2-methyl-5-(methanesulfonyloxy)benzoxazole, 2-methyl-5-(methanesulfonyloxy)benzothiazole, and phenyldiazonium tetrafluoroborate.

As the compound (1), preferred is a compound represented by the formula (4):

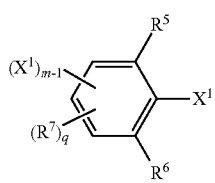

(4)

wherein $X^1$ and m are the same as defined above, $R^5$ and $R^6$ each independently represent a hydrogen atom, a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, $R^7$ is independently in each occurrence a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, q represents an integer of 0 to (4-m), and herein, $R^5$, $R^6$ or $R^7$ may be bonded with the neighboring substituent to form a ring together with the carbon atom to which it is bonded. In the method of the present invention, if even a compound having a substituent(s) at either ortho position or both ortho positions of the leaving group $X^1$ is used, the coupling reaction successfully proceeds.

In the formula (4), Examples of the C1-C10 alkyl group which may have a fluorine atom, the C3-C10 cycloalkyl group, the hydroxyl group, the C1-C20 alkoxy group, the substituted or unsubstituted C6-C20 aryl group, the substituted or unsubstituted C6-C20 aryloxy group, the substituted or unsubstituted heteroaryl group, the substituted or unsubstituted C6-C20 arylthio group, the cyano group, the substituted or unsubstituted amino group, the substituted or unsubstituted aminocarboxy group, the C1-C10 alkylsulfonylamino group, the C6-C20 arylsulfonylamino group, the C2-C10 alkyl group having an N-substituted imino group at 1-position, the C7-C20 aralkyl group having an N-substituted imino group, the imido group, the C1-C20 aliphatic or aromatic acyl group, the carboxyl group, the C2-C20 alkoxycarbonyl group, the C6-C10 aryloxycarbonyl group, the substituted or unsubstituted aminosulfonyl group and the substituted or unsubstituted carbamoyl group include the same as described above, respectively.

A commercially available compound (1) may be used, and one produced according to known methods may be used.

In the formula of the compound represented by the formula (2):

$$R^2\{B(X^2)_2\}_n \qquad (2)$$

(hereinafter, simply referred to as the compound (2)), $R^2$ represents a substituted or unsubstituted n-valent aromatic group, a substituted or unsubstituted n-valent heteroaromatic group, or a substituted or unsubstituted n-valent aliphatic hydrocarbon group having at least one double bond, $X^2$ independently represents a hydroxyl group or an alkoxy group, or two $X^2$ may be bonded to a ring containing a boron atom, and a group represented by $—B(X^2)_2$ are bonded to a sp$^2$ carbon, n represents 1 or 2, with the proviso that when m is 2, n is 1.

Examples of the above-mentioned substituted or unsubstituted n-valent aromatic group include the same as the substituted or unsubstituted m-valent aromatic group. Examples of the substituted or unsubstituted n-valent heteroaromatic group include the same as the above-mentioned substituted or unsubstituted m-valent heteroaromatic group. Examples of the substituted or unsubstituted n-valent aliphatic hydrocarbon group having at least one double bond include the same as the above-mentioned substituted or unsubstituted m-valent aliphatic hydrocarbon group having at least one double bond.

Examples of the alkoxy group represented by $X^2$ include a C1-C10 alkoxy group such as a methoxy group and an ethoxy group. When two $X^2$ are bonded to a ring containing a boron atom, Examples of the group represented by $—B(X^2)_2$ include the groups represented by the followings.

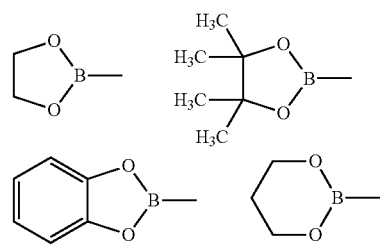

-continued

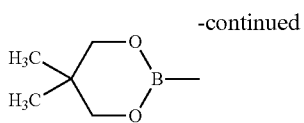

$X^2$ is preferably a hydroxyl group.

When $X^2$ is a hydroxyl group, the compound (2) may be an anhydride form represented by the following formula.

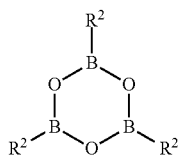

Examples of the compound (2) include phenylboronic acid, o-tolylboronic acid, m-tolylboronic acid, p-tolylboronic acid, 2,3-dimethylphenylboronic acid, 2,4-dimethylphenylboronic acid, 2,5-dimethylphenylboronic acid, 2,6-dimethylphenylboronic acid, 2,4,6-trimethylphenylboronic acid, 2,3,5,6-tetramethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluoromethylphenylboronic acid, 3,5-bis(trifluoromethyl)phenylboronic acid, 2-methoxyphenylboronic acid, 3-methoxyphenylboronic acid, 4-methoxyphenylboronic acid, 2,4-dimethoxyphenylboronic acid, 2,5-dimethoxyphenylboronic acid, 2,6-dimethoxyphenylboronic acid, 3,4-dimethoxyphenylboronic acid, 2-ethoxyphenylboronic acid, 3-ethoxyphenylboronic acid, 4-ethoxyphenylboronic acid, 2-(benzyloxy)phenylboronic acid, 2-phenoxyphenylboronic acid, 4-phenoxyphenylboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 2,6-difluorophenylboronic acid, 3,4-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 2-acetylphenylboronic acid, 3-acetylphenylboronic acid, 4-acetylphenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-diethylaminomethyl)phenylboronic acid, furan-2-boronic acid, furan-3-boronic acid, 5-formylfuran-2-boronic acid, 3-formylfuran-2-boronic acid, benzofuran-2-boronic acid, dibenzofuran-4-boronic acid, thiophene-2-boronic acid, thiophene-3-boronic acid, 4-methylthiophene-2-boronic acid, 5-methylthiophene-2-boronic acid, 5-chlorothiophene-2-boronic acid, 2-acetylthiophene-5-boronic acid, 3-formylthiophene-2-boronic acid, benzothiophene-2-boronic acid, dibenzothiophene-4-boronic acid, pyrazole-4-boronic acid, 3-methylpyrazole-4-boronic acid, 3,5-dimethylpyrazole-4-boronic acid, thiazole-2-boronic acid, pyridine-3-boronic acid, pyridine-4-boronic acid, pyrimidine-5-boronic acid, quinoline-8-boronic acid, isoquinoline-4-boronic acid, 1,4-benzenediboronic acid, 4,4'-biphenyldiboronic acid, vinylboronic acid and 3-methyl-2-beten-2-ylboronic acid.

As the compound (2), a compound represented by the formula (5):

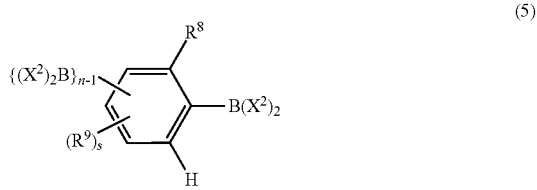

wherein $X^2$ and n are the same as defined above, $R^8$ represents a hydrogen atom, a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, $R^9$ represents a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, s represents an integer of 0 to (4-n), and herein, $R^8$ or $R^9$ may be bonded with the neighboring substituent to form a ring together with the carbon atom to which it is bonded, is preferable. In the method of the present invention, even if a compound having a substituent at ortho position of the group represented by $—B(X_2)_2$ is used, the coupling reaction successfully proceeds.

In the formula (5), examples of the C1-C10 alkyl group which may have a fluorine atom, the C3-C10 cycloalkyl group, the C1-C20 alkoxy group, the substituted or unsubstituted C6-C20 aryl group, the substituted or unsubstituted C6-C20 aryloxy group, the substituted or unsubstituted heteroaryl group, the substituted or unsubstituted C6-C20 arylthio group, the substituted or unsubstituted amino group, the substituted or unsubstituted aminocarboxy group, the C1-C10 alkylsulfonylamino group, the C6-C20 arylsulfonylamino group, the C2-C10 alkyl group having an N-substituted imino group at 1-position, the C7-C20 aralkyl group having an N-substituted imino group, the imido group, the C1-C20 aliphatic, or aromatic acyl group, the C2-C20 alkoxycarbonyl group, the C6-C10 aryloxycarbonyl group, the substituted or unsubstituted aminosulfonyl group and the substituted or unsubstituted carbamoyl group include the same as described above, respectively.

A commercially available compound (2) may be used, and one produced according to known methods may be used.

The reaction of the compound (1) and the compound (2) is carried out in the presence of
(a) at least one nickel compound selected from the group consisting of a nickel carboxylate, nickel nitrate and a nickel halide (hereinafter, simply referred to as the nickel compound (a)),
(b) a phosphine compound represented by the formula (A):

(A)

wherein $R^3$ is independently in each occurrence a C3-C7 alkyl group or a C3-C7 cycloalkyl group, and p represents 2, 3 or 4 (hereinafter, simply referred to as the phosphine (A)),
(c) at least one amine (hereinafter, simply referred to as the amine (c)) selected from the group consisting of a primary amine and an amine represented by the formula (B):

(B)

wherein $R^4$ is independently in each occurrence a substituted or unsubstituted C1-C10 alkyl group, and r represents an integer of 1 to 6 (hereinafter, simply referred to as the amine (B)), and
(d) an inorganic base.

Examples of the nickel carboxylate include a C2-C20 nickel carboxylate such as nickel acetate, nickel stearate, nickel cyclohexanebutyrate, nickel 2-ethylhexanoate and nickel naphthenate, and examples of the nickel halide include nickel chloride and nickel bromide.

As the nickel compound (a), a C2-C12 nickel carboxylate is preferable, and nickel acetate, nickel stearate, nickel cyclohexanebutyrate, nickel 2-ethylhexanoate and nickel naphthenate are more preferable.

The nickel compound (a) may be its anhydride or its hydrate. Additionally, the nickel compound (a) may be supported on a support such as carbon, silica and alumina.

Two or more kinds of the nickel compound (a) may be used in combination.

The amount of the nickel compound (a) to be used is usually 0.001 to 100 mol % per 1 mole of the compound (1), and preferably 0.001 to 20 mol %.

In the formula of the phosphine (A), $R^3$ is independently in each occurrence a C3-C7 alkyl group or a C3-C7 cycloalkyl group, and p represents 2, 3 or 4.

Examples of the C3-C7 alkyl group include an n-propyl group, an isopropyl group, an n-butyl group, a tert-butyl group and an n-hexyl group, and examples of the C3-C7 cycloalkyl group include a cyclopentyl group, a cyclohexyl group and a 2-norbornyl group. Among them, preferred is a C3-C7 cycloalkyl group, and more preferred is a cyclohexyl group. The phosphine (A) wherein p is 4 is preferable.

As the phosphine (A), 1,2-bis(dicyclohexylphosphino) ethane, 1,3-bis(dicyclohexylphosphino)propane and 1,4-bis (dicyclohexylphosphino)butane are preferable, and 1,4-bis (dicyclohexylphosphino)butane is more preferable. Two or more kinds of the phosphine (A) may be used in combination.

The amount of the phosphine (A) to be used is usually 0.05 to 4 moles per 1 mole of nickel atom, and preferably 0.1 to 3 moles.

In the present invention, "aliphatic primary amine" means a compound wherein one hydrogen atom of ammonia is replaced by linear or branched chain aliphatic hydrocarbon group which may have a substituent or an alicyclic hydrocarbon group which may have a substituent. Examples of the substituent include a C6-C20 aryl group such as a phenyl group and a di-substituted amino group such as a dimethylamino group.

As the aliphatic primary amine, a C1-C20 aliphatic primary amine is preferable, and examples thereof include ethylamine, n-propylamine, isopropylamine, n-butylamine, isobutylamine, sec-butylamine, tert-butylamine, n-pentylamine, isopentylamine, neopentylamine, sec-pentylamine, n-hexylamine, tert-octylamine, n-undecylamine, 4-phenylbutylamine, cyclohexylamine, benzylamine and N,N-dimethyl-1,2-ethanediamine.

In the formula (B), examples of the substituted or unsubstituted C1-C10 alkyl group include a methyl group, an ethyl group, an n-propyl group, an isopropyl group and an n-butyl group.

Examples of the amine (B) include N,N,N',N'-tetramethylmethanediamine, N,N,N',N'-tetraethylmethanediamine, N,N,N',N'-tetramethyl-1,2-ethanediamine, N,N,N',N'-tetraethyl-1,2-ethanediamine, N,N,N',N'-tetra-n-propyl-1,2-ethanediamine, N,N,N',N'-tetraisopropyl-1,2-ethanediamine, N,N,N',N'-tetra-n-butyl-1,2-ethanediamine, N,N,N', N'-tetramethyl-1,3-propanediamine, N,N,N',N'-tetraethyl-1, 3-propanediamine, N,N,N',N'-tetramethyl-1,4-butanediamine, N,N,N',N'-tetramethyl-1,5-pentanediamine, N,N,N',N'-tetramethyl-1,6-hexanediamine and N,N,N',N'-tetrabutyl-1,6-hexanediamine.

As the amine (c), an aliphatic primary amine is preferable, and n-butylamine is more preferable.

Two or more kinds of the aliphatic primary amine may be used in combination, two or more kinds of the amine (B) may be used in combination, and one or more aliphatic primary amines may be used in combination with one or more amine (B).

The amount of the amine (c) to be used is usually 0.1 to 30 moles per 1 mole of nickel atom, and preferably 0.3 to 15 moles.

Examples of the inorganic base include an alkali metal hydroxide, an alkaline earth metal hydroxide, an alkali metal carbonate, an alkaline earth metal carbonate, an alkali metal hydrogen carbonate, an alkali metal phosphate, an alkaline earth metal phosphate, an alkali metal carboxylate, an alkaline earth metal carboxylate, an alkali metal alkoxide and an alkaline earth metal alkoxide.

Examples of the alkali metal hydroxide include lithium hydroxide, sodium hydroxide and potassium hydroxide. Examples of the alkaline earth metal hydroxide include calcium hydroxide, magnesium hydroxide and barium hydroxide. Examples of the alkali metal carbonate include lithium carbonate, sodium carbonate, potassium carbonate and cesium carbonate. Examples of the alkaline earth metal carbonate include calcium carbonate and barium carbonate: Examples of the alkali metal hydrogen carbonate include sodium hydrogen carbonate and potassium hydrogen carbonate. Examples of the alkali metal phosphate include lithium phosphate, sodium phosphate and potassium phosphate. Examples of the alkaline earth metal phosphate include calcium phosphate. Examples of the alkali metal carboxylate include sodium acetate. Examples of the alkaline earth metal carboxylate include calcium carbonate. Examples of the alkali metal alkoxide include sodium methoxide, sodium tert-butoxide and potassium tert-butoxide. Examples of the alkaline earth metal alkoxide include magnesium ethoxide.

Among them, preferred are an alkali metal hydroxide, an alkaline earth metal hydroxide, an alkali metal carbonate, an alkaline earth metal carbonate, an alkali metal hydrogen carbonate, an alkali metal phosphate, an alkaline earth metal phosphate, an alkali metal carboxylate and an alkaline earth metal carboxylate, more preferred are an alkali metal hydroxide, an alkaline earth metal hydroxide, an alkali metal carbonate, an alkaline earth metal carbonate, an alkali metal phosphate and an alkaline earth metal phosphate, and especially preferred is an alkali metal phosphate. Two or more kinds of the inorganic base may be used in combination.

The amount of the inorganic base to be used is usually 0.1 to 15 moles per 1 mole of the compound (2), and preferably 1 to 10 moles.

In the present reaction, the compound (2) wherein the amount of the boron atom in the compound (2) is 1 mole or more per 1 mole of the leaving group in the compound (1) may be used, and the compound (1) wherein the amount of the leaving group in the compound (1) is 1 mole or more per 1 mole of the boron atom in the compound (2) may be used. The compound (2) wherein the amount of the boron atom in the compound (2) is 1 mole or more per 1 mole of the leaving group in the compound (1) is preferably used, and the compound (2) wherein the amount of the boron atom in the compound (2) is 1 to 2 moles is more preferably used.

The reaction of the compound (1) and the compound (2) is usually conducted in a solvent. Examples of the solvent include water and an organic solvent, and the organic solvent is preferable. Examples of the organic layer include an alcohol solvent such as methanol and ethanol, an aprotic polar solvent such as N-methylpyrrolidone, N,N-dimethylformamide, N,N-dimethylacetamide, acetonitrile, benzonitrile and dimethylsulfoxide, an ether solvent such as diethyl ether, tert-butyl methyl ether, 1,2-dimethoxyethane, 1,4-dioxane, tetrahydrofuran and anisole, an aromatic hydrocarbon solvent such as benzene, toluene and xylene, and an aliphatic hydrocarbon solvent such as hexane and heptane. Among them, preferred is an ether solvent. Two or more kinds of the solvent may be used in combination.

The amount of the solvent to be used is usually 0.5 to 700 parts by weight per 1 part by weight of the compound (1), and preferably 1 to 500 parts by weight.

The reaction temperature is usually 0 to 200° C. and preferably 20 to 180° C.

While the reaction pressure is not limited, it is usually normal pressure.

The reaction time is not limited, and the point where either the compound (1) or the compound (2) is disappeared can be set as the ending point of the reaction. It is usually 1 minute to 72 hours.

The reaction is preferably conducted under an atmosphere of an inert gas such as nitrogen and argon.

The reaction is usually carried out by mixing the compound (1), the compound (2), the nickel compound (a), the phosphine (A), the amine (c), the inorganic base and if necessary, the solvent, and the mixing order is not limited. The nickel compound (a) may be perfectly dissolved or be suspended in the reaction mixture.

After completion of the reaction, an unsaturated organic compound represented by the formula (3):

$(Y^1)_{m-1}-R^1-R^2-(Y^2)_{n-1}$ (3)

wherein $R^1$, $R^2$, m and n are the same as defined above, $Y^1$ represents $R^2$ or $X^1$, $Y^2$ represents $R^1$ or $B(X^2)_2$, $X^1$ and $X^2$ are the same as defined above (hereinafter, simply referred to as the compound (3)) can be isolated, for example, by acidifying the obtained reaction mixture using an acidic aqueous solution such as diluted hydrochloric acid, diluted sulfuric acid and an aqueous ammonium chloride solution, extracting if necessary, by adding an water-insoluble organic solvent and washing the obtained organic layer followed by concentration. The isolated compound (3) may be further purified by a conventional purification means such as distillation, recrystallization and various chromatography.

Examples of the water-insoluble organic solvent include an aromatic hydrocarbon solvent such as toluene and xylene, an ester solvent such as ethyl acetate, an ether solvent such as diethyl ether, a ketone solvent such as methyl tert-butyl ketone, and a halogenated hydrocarbon solvent such as chloroform, dichloromethane and dichloroethane, and the amount thereof to be used is not limited.

Examples of the compound (3) include biphenyl, 2,5-dimethylbiphenyl, 4-methoxybiphenyl, 4-methoxy-2'-methylbiphenyl, 4-methoxy-3'-methylbiphenyl, 4-methoxy-4'-methylbiphenyl, 4-tert-butyl-3'-methylbiphenyl, methyl 3-(3,5-difluorophenyl)phenylacetate, 4-isopropyl-4'-methylbiphenyl, 3-ethoxycarbonyl-4'-acetylbiphenyl, 4-methoxy-3'-methoxybiphenyl, 4-(N,N-dimethylamino)-3'-trifluorobiphenyl, 3,5-difluoro-3',5'-dimethylbiphenyl, 4-formylbiphenyl, 2,4-difluorobiphenyl, 2-methylstyrene, 2-ethoxy-3'-carboxybiphenyl, 2-fluoro-4-phenyl-4'-tert-butylbiphenyl, 3-methoxy-2',4',6'-trimethylbiphenyl, 2,6-dimethoxybiphenyl, 2-methoxy-3'-trifluoromethylbiphenyl, 2,6-dimethoxy-3-(N,N-diethylamino)biphenyl, 2-(2-ethoxyphenyl)benzonitrile, 3-fluoro-2',4',6'-trimethylbiphenyl, 2,5-dimethyl-4'-carboxylbiphenyl, 2,5-dimethyl-2'-cyanobiphenyl, 2,5-dimethyl-4'-trifluoromethylbiphenyl, 2-methoxy-2'-cyanobiphenyl, 2,6-dimethoxy-4'-trifluoromethylbiphenyl, 2-phenylbenzofuran, 2-(3,5-difluorophenyl)naphthalene, 2-vinylnaphthalene, 2-(2,4,6-trimethylphenyl)naphthalene, 9,10-diphenylanthracene, 9-(3-cyanophenyl)-10-(2-ethoxyphenyl)anthracene, 2-(2-ethoxyphenyl)fluorene, 4-(2,5-difluorophenyl)benzaldehyde, 2,4,6-trimethylbiphenyl, 2,6,2'-trimethylbiphenyl, 2,6,2'-triethylbiphenyl, 2-ethyl-2',6'-dimethylbiphenyl, 2,6-dimethyl-2'-methoxybiphenyl, 2,6-dimethyl-2'-ethoxybiphenyl, 2-fluoro-2',6'-dimethylbiphenyl, 2,4-difluoro-2',6'-dimethylbiphenyl, 2-cyano-2',6'-dimethylbiphenyl, 2-cyano-4-benzyl-2',6'-dimethylbiphenyl, 2-trifluoro-2',6'-dimethylbiphenyl, 2-trifluoro-3-formyl-2',6'-dimethylbiphenyl, 2-phenyl-2',6'-dimethylbiphenyl, 2-(3-(N,N-diethylamino)phenyl)-2',6'-dimethylbiphenyl, 2-(3-(N,N-dimethylamino)phenyl)toluene, 2-(3-thienyl)-2',6'-dimethylbiphenyl, 2-(2,6-dimethylphenyl)acetophenone, 2-(2-ethyl-6-methylphenyl)acetophenone, 2-(2-ethoxy-6-methylphenyl)-4-(3-pyridyl)acetophenone, 2-(2-fluoro-6-methoxyphenyl)benzophenone, 2-(2-cyano-6-methoxyphenyl)-5-formylbenzophenone, 2,6-dimethyl-2'-methoxy-4'-(3- pyridyl)biphenyl, 2-ethyl-6-ethoxy-2'-methylbiphenyl, 2-ethyl-6-ethoxy-2',3'-dimethylbiphenyl, 2,4,6-trimethyl-4'-trifluoromethylbiphenyl, 1-(2,6-dimethylphenyl)naphthalene, 2-(2,6-dimethylphenyl)naphthalene, 1-methyl-4-(2,6-dimethylphenyl)imidazole, 1-phenyl-5-(2,4-diethyl-6-fluorophenyl)imidazole, 2-(2,6-dimethylphenyl)thiophene, 3-(2,6-diethylphenyl)thiophene, 2-(2,6-dimethylphenyl)benzothiophene, 3-(2-ethyl-6-methylphenyl)benzothiophene, 2-(2,6-dimethylphenyl)furan, 3-(2,6-dimethoxyphenyl)furan, 2-(2-ethyl-6-methylphenyl)benzofuran, 3-(2,6-dimethylphenyl)benzofuran, 2-ethyl-3-(2,6-dimethylphenyl)pyridine, 2-phenyl-3-(2,6-dimethylphenyl)pyridine, 2-cyano-3-(2,6-dimethylphenyl)pyridine, 3-(2,6-diethylphenyl)-4-picoline, 3-(2,6-diethylphenyl)-4-cyanopyridine, 2-phenyl-3-picoline, 2-(3-cyanophenyl)pyridine, 2-vinyl-6-(2-methylphenyl)pyridine, 3-phenyl-5-(3-carboxyphenyl)pyridine, 5-phenyl-1-methylimidazole, 5-(N,N-dimethylaminophenyl)-1-methylimidazole, 1-methyl-5-(3-pyridyl)imidazole, 2-(4-acetylphenyl)thiophene, 2-(3-pyridyl)benzothiophene and 1-vinyl-2,5-difluorobenzene.

EXAMPLES

The present invention will be illustrated below by Examples in more detail, but the present invention is not limited to these Examples.

Example 1

To a glass reaction container equipped with a condenser, 12.4 mg of nickel acetate tetrahydrate, 22.5 mg of 1,4-bis(dicyclohexylphosphino)butane, 21.9 mg of n-butylamine, 140.6 mg of 1-chloro-2,6-dimethylbenzene, 176.8 mg of o-tolylboronic acid, 424.6 mg of potassium phosphate and 3.5 mL of 1,2-dimethoxyethane were added. The obtained mixture was heated and stirred at 100° C. for 8 hours, and then, the reaction mixture was cooled down to room temperature, and 50 mL of aqueous saturated ammonium chloride solution and 50 mL of ethyl acetate were added thereto. The obtained mixture was separated to an organic layer and an aqueous layer. The obtained organic layer was washed with 50 mL of aqueous saturated sodium chloride solution. The obtained organic layer was dried over anhydrous magnesium sulfate and then, the filtration was conducted to obtain a solution containing 2,6,2'-trimethylbiphenyl. The solution was analyzed with gas chromatography internal standard method (internal standard: n-undecane) to find that the yield of 2,6,2'-trimethylbiphenyl was 76%.

$^1$H-NMR (δ: ppm, CDCl$_3$) 7.00-7.27 (c, 7H), 1.97 (s, 3H), 1.94 (s, 6H)

GC-MS (m/z) 196 (M$^+$)

Example 2

The reaction was conducted according to the same manner as Example 1 except that 30.4 mg of n-hexylamine was used in place of n-butylamine to obtain a solution containing 2,6,2'-trimethylbiphenyl. Yield: 76%.

Example 3

The reaction was conducted according to the same manner as Example 1 except that 47.2 mg of n-decylamine was used in place of n-butylamine to obtain a solution containing 2,6,2'-trimethylbiphenyl. Yield: 77%.

Example 4

The reaction was conducted according to the same manner as Example 1 except that 51.4 mg of n-undecylamine was used in place of n-butylamine to obtain a solution containing 2,6,2'-trimethylbiphenyl. Yield: 74%.

Example 5

The reaction was conducted according to the same manner as Example 1 except that 44.8 mg of 4-phenylbutylamine was used in place of n-butylamine to obtain a solution containing 2,6,2'-trimethylbiphenyl. Yield: 63%.

Example 6

The reaction was conducted according to the same manner as Example 1 except that 38.8 mg of N,N-dimethyl-1,2-ethanediamine was used in place of n-butylamine to obtain a solution containing 2,6,2'-trimethylbiphenyl. Yield: 62%.

Comparative Example 1

Under argon flow, to a Schlenk tube, 473 mg of 30% by weight aqueous sodium triphenylphosphinotrimethasulfonate solution, 16.4 mg of zinc powder, 26.4 mg of dichloro[1,2-bis(diphenylphosphino)ethane]nickel and 0.3 mL of water were added. The obtained mixture was heated and stirred at 80° C. for 2 hours. The obtained mixture was cooled down to 50° C., and 1 mL of a 1,4-dioxane solution containing 74.8 mg of o-tolylboronic acid, 70.3 mg of 1-chloro-2,6-dimethylbenzene and 0.4 mL of 3.7 M aqueous potassium phosphate solution were added thereto. The obtained mixture was heated and stirred at 50° C. for 8 hours. The obtained mixture was cooled down to room temperature, and 7 mL of aqueous saturated ammonium chloride solution was added thereto followed by extracting three times with 20 mL of diethyl ether. The obtained organic layers were mixed to wash with 20 mL of aqueous saturated sodium chloride solution. The obtained organic layer was dried over anhydrous magnesium sulfate and then, the filtration was conducted to obtain a solution. The solution was analyzed with gas chromatography internal standard method (internal standard: n-undecane) and the generation of 2,6,2'-trimethylbiphenyl was not able to be confirmed.

Comparative Example 2

The reaction was conducted according to the same manner as Example 1 except that n-butylamine was not used, but 2,6,2'-trimethylbiphenyl was not generated.

Comparative Example 3

The reaction was conducted according to the same manner as Example 1 except that 1,4-bis(dicyclohexylphosphino)butane was not used, but 2,6,2'-trimethylbiphenyl was not generated.

Comparative Example 4

The reaction was conducted according to the same manner as Example 1 except that potassium phosphate was not used, and a solution containing 2,6,2'-trimethylbiphenyl was obtained. Yield: 3%.

Example 7

The reaction was conducted according to the same manner as Example 1 except that heating and stirring time was 3 hours, and a solution containing 2,6,2'-trimethylbiphenyl was obtained. Yield: 57%.

Comparative Example 5

The reaction was conducted according to the same manner as Example 7 except that 38.8 mg of di(n-butyl)amine was used in place of n-butylamine to obtain a solution containing 2,6,2'-trimethylbiphenyl. Yield: 4%.

Comparative Example 6

The reaction was conducted according to the same manner as Example 7 except that 55.6 mg of tri(n-butyl)amine was used in place of n-butylamine to obtain a solution containing 2,6,2'-trimethylbiphenyl. Yield: 2%.

Comparative Example 7

The reaction was conducted according to the same manner as Example 7 except that n-butylamine was not used, but 2,6,2'-trimethylbiphenyl was not generated.

Comparative Example 8

The reaction was conducted according to the same manner as Example 7 except that 26.2 mg of triphenylphosphine was used in place of 1,4-bis(dicyclohexylphosphino)butane to obtain a solution containing 2,6,2'-trimethylbiphenyl. Yield: 3%.

Comparative Example 9

The reaction was conducted according to the same manner as Example 7 except that 28.0 mg of tricyclohexylphosphine was used in place of 1,4-bis(dicyclohexylphosphino) butane to obtain a solution containing 2,6,2'-trimethylbiphenyl. Yield: 11%.

Example 8

The reaction was conducted according to the same manner as Example 1 except that 14.5 mg of nickel nitrate hexahydrate was used in place of nickel acetate tetrahydrate to obtain a solution containing 2,6,2'-trimethylbiphenyl. Yield: 51%.

Example 9

The reaction was conducted according to the same manner as Example 1 except that 31.3 mg of nickel stearate was used in place of nickel acetate tetrahydrate to obtain a solution containing 2,6,2'-trimethylbiphenyl. Yield: 61%.

Example 10

The reaction was conducted according to the same manner as Example 1 except that 6.5 mg of nickel chloride was used in place of nickel acetate tetrahydrate to obtain a solution containing 2,6,2'-trimethylbiphenyl. Yield: 56%.

Example 11

The reaction was conducted according to the same manner as Example 1 except that 12.3 mg of nickel bromide hydrate, which was a mixture of monohydrate and dihydrate, was used in place of nickel acetate tetrahydrate to obtain a solution containing 2,6,2'-trimethylbiphenyl. Yield: 55%.

Example 12

The reaction was conducted according to the same manner as Example 1 except that 15.4 mg of nickel bromide-ethylene glycol dimethyl ether complex was used in place of nickel acetate tetrahydrate to obtain a solution containing 2,6,2'-trimethylbiphenyl. Yield: 49%.

Example 13

The reaction was conducted according to the same manner as Example 1 except that 3.5 mL of anisole was used in place of 1,2-dimethoxyethane to obtain a solution containing 2,6,2'-trimethylbiphenyl. Yield: 54%.

Example 14

The reaction was conducted according to the same manner as Example 1 except that the amount of o-tolylboronic acid was 203.9 mg to obtain a solution containing 2,6,2'-trimethylbiphenyl. Yield: 82%.

Example 15

The reaction was conducted according to the same manner as Example 1 except that 254.2 mg of 2,6-dimethylphenyl trifluoromethanesulfonate was used in place of 1-chloro-2,6-dimethylbenzene to obtain a solution containing 2,6,2'-trimethylbiphenyl. Yield: 87%.

Example 16

The reaction was conducted according to the same manner as Example 15 except that the heating and stirring time was 3 hours to obtain a solution containing 2,6,2'-trimethylbiphenyl. Yield: 63%.

Examples 17 to 35

To a glass reaction container equipped with a condenser, 0.05 mmol of nickel acetate tetrahydrate, 0.05 mmol of 1,4-bis(dicyclohexylphosphino)butane, 0.3 mmol of n-butylamine, 1 mmol of the compound (1) represented in Table 1 and Table 2, 1.3 mmol of the compound (2) represented in Table 1 and Table 2, 2 mmol of potassium phosphate and 3.5 mL of 1,2-dimethoxyethane were added. The obtained mixture was heated and stirred at 100° C. for 8 hours. The obtained reaction mixture was cooled down to room temperature, and 50 mL of aqueous saturated ammonium chloride solution and 50 mL of ethyl acetate were added thereto. The obtained mixture was separated to an organic layer and an aqueous layer. The obtained organic layer was washed with 50 mL of aqueous saturated sodium chloride solution, and then, dried over anhydrous magnesium sulfate followed by conducting the filtration to obtain a solution containing the desired compound (3). The yield of the compound (3) was calculated by analyzing the obtained solution as it is with gas chromatography internal standard method or by concentrating the obtained solution followed by purifying the obtained crude product with silica gel chromatography. The results are shown in Table 1 and Table 2.

TABLE 1
| Example | Compound (1) | Compound (2) | Compound (3) | Yield (%) |
|---|---|---|---|---|
| 17 | 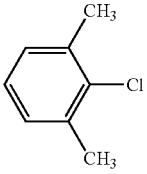 | 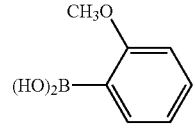 | 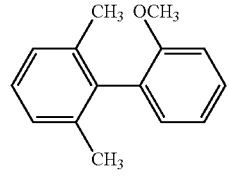 | 56 |
| 18 | 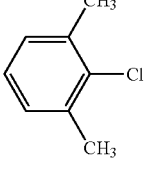 | 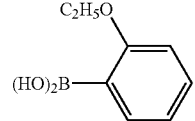 | 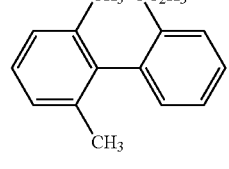 | 73 |
| 19 | 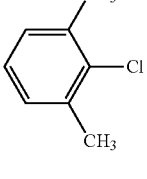 | 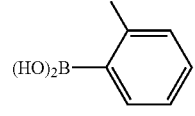 | 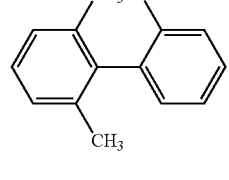 | 32 |
| 20 | 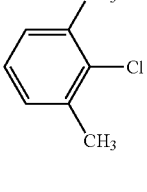 | 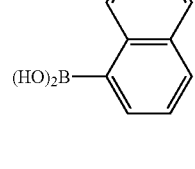 | 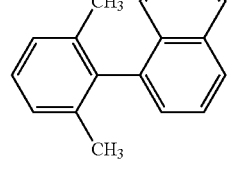 | 69 |
| 21 | 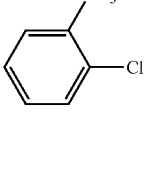 | 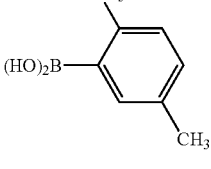 | 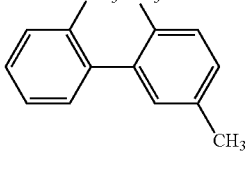 | 100 |
| 22 | 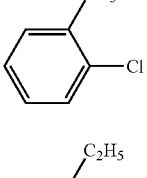 | 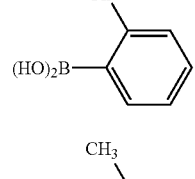 | 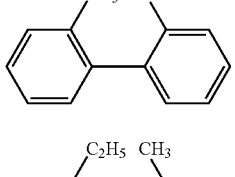 | 57 |
| 23 | 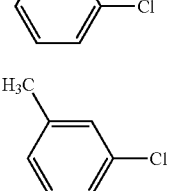 | 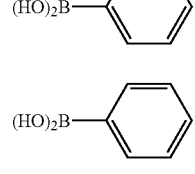 | 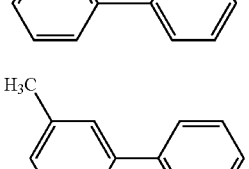 | 90 |
| 24 | 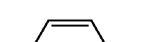 | 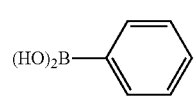 | 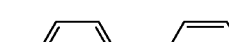 | 100 |
| 25 |  |  |  | 91 |

TABLE 1-continued

| Example | Compound (1) | Compound (2) | Compound (3) | Yield (%) |
|---|---|---|---|---|
| 26 | NC–C₆H₄–Cl | (HO)₂B–Ph | NC–C₆H₄–Ph | 96 |
| 27 | OHC–C₆H₄–Cl | (HO)₂B–Ph | OHC–C₆H₄–Ph | 66 |

TABLE 2

| Example | Compound (1) | Compound (2) | Compound (3) | Yield (%) |
|---|---|---|---|---|
| 28 | 3-H₂N-C₆H₄-Cl | (HO)₂B–Ph | 3-H₂N-C₆H₄-Ph | 95 |
| 29 | 4-H₂N-C₆H₄-Cl | (HO)₂B–C₆H₄–Ph | H₂N–C₆H₄–C₆H₄–Ph | 81 |
| 30 | C₆H₅–Cl | (HO)₂B-(3-thienyl) | 3-phenylthiophene | 85 |
| 31 | C₆H₅–Br | (HO)₂B-(3-thienyl) | 3-phenylthiophene | 69 |
| 32 | 10-chloroanthracene | 2-CH₃-C₆H₄-B(OH)₂ | 10-(2-methylphenyl)anthracene | 93 |
| 33 | 10-bromoanthracene | 2-CH₃-C₆H₄-B(OH)₂ | 10-(2-methylphenyl)anthracene | 84 |

TABLE 2-continued

| Example | Compound (1) | Compound (2) | Compound (3) | Yield (%) |
|---|---|---|---|---|
| 34 | 3-methyl-2-chlorothiophene | o-tolylboronic acid | 2-(2-methylphenyl)-3-methylthiophene | 67 |
| 35 | 8-chloroquinoline | o-tolylboronic acid | 8-(2-methylphenyl)quinoline | 78 |

The spectral data of the compound (3) obtained in Example 17 is as followed:

$^1$H-NMR (δ: ppm, CDCl$_3$) 7.34 (m, 1H), 7.03-7.19 (c, 3H), 6.96-7.03 (c, 3H), 3.73 (s, 3H), 2.01 (s, 6H)

$^{13}$C-NMR (δ: ppm, CDCl$_3$) 156.50, 138.19, 136.58, 130.64, 129.49, 128.35, 127.04, 127.00, 120.65, 110.84, 55.41, 20.44

GC-MS (m/z) 212 (M$^+$)

The spectral data of the compound (3) obtained in Example 18 is as followed:

$^1$H-NMR (δ: ppm, CDCl$_3$) 7.27-7.34 (m, 1H), 6.95-7.18 (c, 6H), 3.99 (q, 2H), 2.02 (s, 6H), 1.21 (t, 3H)

$^{13}$C-NMR (δ: ppm, CDCl$_3$) 155.76, 138.43, 136.55, 130.83, 130.00, 128.20, 126.88, 126.79, 120.52, 112.23, 63.53, 20.47, 14.70

GC-MS (m/z) 226 (M$^+$)

The spectral data of the compound (3) obtained in Example 19 is as followed:

$^1$H-NMR (δ: ppm, CDCl$_3$) 7.10-7.38 (c, 7H), 2.05 (s, 6H)

GC-MS (m/z) 200 (M$^+$)

The spectral data of the compound (3) obtained in Example 20 is as followed:

$^1$H-NMR (δ: ppm, CDCl$_3$) 7.84-7.92 (c, 2H), 7.16-7.57 (c, 8H), 1.90 (s, 6H)

GC-MS (m/z) 232 (M$^+$)

The spectral data of the compound (3) obtained in Example 21 is as followed:

$^1$H-NMR (δ: ppm, CDCl$_3$) 7.05-7.26 (c, 6H), 6.92 (s, 1H), 2.33 (s, 3H), 2.06 (s, 3H), 2.01 (s, 3H)

GC-MS (m/z) 196 (M$^+$)

The spectral data of the compound (3) obtained in Example 22 is as followed:

$^1$H-NMR (δ: ppm, CDCl$_3$) 6.99-7.47 (c, 13H), 1.90 (s, 3H)

GC-MS (m/z) 244 (M$^+$)

The spectral data of the compound (3) obtained in Example 23 is as followed:

$^1$H-NMR (δ: ppm, CDCl$_3$) 7.07-7.31 (c, 8H), 2.38 (m, 2H), 2.05 (s, 3H), 1.03 (t, 3H)

GC-MS (m/z) 168 (M$^+$-28)

The spectral data of the compound (3) obtained in Example 32 and 33 is as followed:

$^1$H-NMR (δ: ppm, CDCl$_3$) 8.49 (s, 1H), 8.05 (d, 2H), 7.24-7.51 (c, 10H), 1.86 (s, 3H)

GC-MS (m/z) 268 (M$^+$)

The spectral data of the compound (3) obtained in Example 34 is as followed:

$^1$H-NMR (δ: ppm, CDCl$_3$) 7.21-7.27 (c, 5H), 6.19 (d, 1H), 2.20 (s, 3H), 2.04 (s, 3H)

GC-MS (m/z) 188 (M$^+$)

The spectral data of the compound (3) obtained in Example 35 is as followed:

$^1$H-NMR (δ: ppm, CDCl$_3$) 8.90 (m, 1H), 8.19 (dd, 1H), 7.83 (m, 1H), 7.57-7.60 (c, 2H), 7.29-7.39 (c, 5H), 2.04 (s, 3H)

GC-MS (m/z) 219 (M$^+$)

Example 36

To a glass reaction container equipped with a condenser, 12.4 mg of nickel acetate tetrahydrate, 22.5 mg of 1,4-bis(dicyclohexylphosphino)butane and 1 mL of 1,2-dimethoxyethane were added. The obtained mixture was stirred at 20° C. for 30 minutes, and then, 21.9 mg of n-butylamine and 0.5 mL of 1,2-dimethoxyethane were added thereto. The obtained mixture was heated and stirred at 100° C. for 30 minutes to obtain a solution (A).

To a glass reaction container equipped with a condenser, 176.8 mg of o-tolylboronic acid, 424.6 mg of potassium phosphate and 2 mL of 1,2-dimethoxyethane were added. The obtained mixture was stirred at 100° C. for 1 hour, and then, 140.6 mg of 1-chloro-2,6-dimethylbenzene was added thereto and the solution (A) was further added thereto. The obtained mixture was heated and stirred at 100° C. for 8 hours. The obtained reaction mixture was cooled down to room temperature, and 50 mL of aqueous saturated ammonium chloride solution and 50 mL of ethyl acetate were added thereto. The obtained mixture was separated to an organic layer and an aqueous layer. The obtained organic layer was washed with 50 mL of aqueous saturated sodium chloride solution and then, was dried over anhydrous magnesium sulfate followed by conducting the filtration to obtain a solution containing 2,6,2'-trimethylbiphenyl. Yield: 66%.

Example 37

The reaction was conducted according to the same manner as Example 36 except that the heating and stirring time after addition of the solution (A) was 3 hours to obtain a solution containing 2,6,2'-trimethylbiphenyl. Yield: 45%.

Example 38

The reaction was conducted according to the same manner as Example 37 except that 17.4 mg of N,N,N',N'-tetramethyl- 1,2-ethanediamine was used in place of n-butylamine to obtain a solution containing 2,6,2'-trimethylbiphenyl. Yield: 28%.

Comparative Example 10

The substitution inside of a 50 mL flask equipped with a condenser with nitrogen was conducted, and then, 9.7 mg of nickel chloride, 26.7 mg of N,N,N',N'-tetramethyl-1,2-ethanediamine, 78.7 mg of triphenylphosphine and 11.0 g of tetrahydrofuran were added thereto. The obtained mixture was heated under reflux for 30 minutes. The obtained mixture was cooled down to room temperature, and 448.7 mg of o-tolylboronic acid, 421.8 mg of 1-chloro-2,6-dimethylbenzene and 1.24 g of potassium carbonate were added thereto. The obtained mixture was heated under reflux for 3 hours. The obtained reaction mixture was cooled down to room temperature, and 60 mL of aqueous saturated ammonium chloride solution and 60 mL of ethyl acetate were added thereto. The obtained mixture was separated to an organic layer and an aqueous layer. The obtained organic layer was washed with 60 mL of aqueous saturated sodium chloride solution and then, was dried over anhydrous magnesium sulfate followed by conducting the filtration to obtain a solution. The solution was analyzed with gas chromatography internal standard method (internal standard: n-undecane), but the generation of 2,6,2'-trimethylbiphenyl was not confirmed.

INDUSTRIAL APPLICABILITY

According to the present invention, an unsaturated organic compound can be produced in a good yield. Especially, even if a compound having a substituent(s) at either ortho position or both ortho positions of the leaving group $X^1$ or a compound having a substituent at ortho position of the group represented by $—B(X_2)_2$ is used, the desired unsaturated organic compound can be obtained in a good yield, and therefore, the method of the present invention is industrially advantageous.

The invention claimed is:
1. A method for producing an unsaturated organic compound represented by the formula (3):

wherein $R^1$ represents a substituted or unsubstituted m-valent aromatic group, a substituted or unsubstituted m-valent heteroaromatic group, or a substituted or unsubstituted m-valent aliphatic hydrocarbon group having at least one double bond, $R^2$ represents a substituted or unsubstituted n-valent aromatic group, a substituted or unsubstituted n-valent heteroaromatic group, or a substituted or unsubstituted n-valent aliphatic hydrocarbon group having at least one double bond, m represents 1 or 2, n represents 1 or 2, with the proviso that when m is 2, n is 1, $Y^1$ represents $R^2$ or $X^1$, $Y^2$ represents $R^1$ or $B(X^2)_2$, $X^1$ independently represents a leaving group bonded to a sp² carbon, $X^2$ independently represents a hydroxyl group or an alkoxy group, or two $X^2$ are bonded to a ring containing a boron atom, and a group represented by $—B(X^2)_2$ are bonded to a sp² carbon,
which comprises reacting a compound represented by the formula (1):

wherein $R^1$, $X^1$ and m are the same as defined above, with a compound represented by the formula (2):

wherein $R^2$, $X^2$ and n are the same as defined above, in the presence of (a) at least one nickel compound selected from the group consisting of a nickel carboxylate, nickel nitrate and a nickel halide,
(b) a phosphine compound represented by the formula (A):

wherein $R^3$ is independently in each occurrence a C3-C7 alkyl group or a C3-C7 cycloalkyl group, and p represents 2, 3 or 4,
(c) at least one amine selected from the group consisting of a primary amine and an amine represented by the formula (B):

wherein $R^4$ is independently in each occurrence a substituted or unsubstituted C1-C10 alkyl group, and r represents an integer of 1 to 6, and
(d) an inorganic base.
2. The method according to claim 1, wherein the compound represented by the formula (1) is a compound represented by the formula (4):

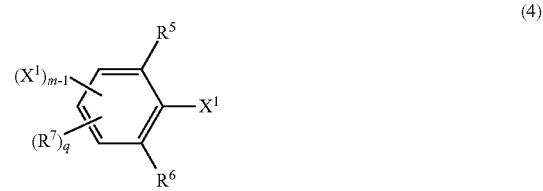

wherein $X^1$ and m are the same as defined above, $R^5$ and $R^6$ each independently represent a hydrogen atom, a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group,
$R^7$ is independently in each occurrence a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, q represents an integer of 0 to (4-m), and herein, $R^5$, $R^6$ or $R^7$ may be bonded with the neighboring substituent to form a ring together with the carbon atom to which it is bonded.

3. The method according to claim 1, wherein the compound represented by the formula (2) is a compound represented by the formula (5):

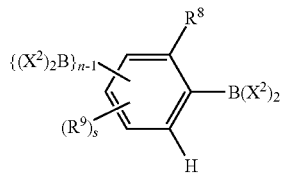

(5)

wherein $X^2$ and n are the same as defined above, $R^8$ represents a hydrogen atom, a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, $R^9$ represents a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, s represents an integer of 0 to (4-n), and herein, $R^8$ or $R^9$ may be bonded with the neighboring substituent to form a ring together with the carbon atom to which it is bonded.

4. The method according to claim 1, wherein the nickel carboxylate is nickel acetate and the nickel halide is nickel chloride or nickel bromide.

5. The method according to claim 1, wherein $R^3$ is a C3-C7 cycloalkyl group.

6. The method according to claim 5, wherein $R^3$ is a cyclohexyl group.

7. The method according to claim 1, wherein p is 4.

8. The method according to claim 1, wherein at least one amine selected from the group consisting of a primary amine and an amine represented by the formula (B) is an aliphatic primary amine.

9. The method according to claim 2, wherein the compound represented by the formula (2) is a compound represented by the formula (5):

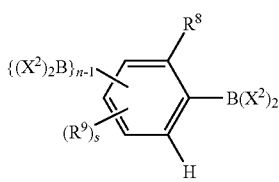

(5)

wherein $X^2$ and n are the same as defined above, $R^8$ represents a hydrogen atom, a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, $R^9$ represents a fluorine atom, a C1-C10 alkyl group which may have a fluorine atom, a C3-C10 cycloalkyl group, a hydroxyl group, a C1-C20 alkoxy group, a substituted or unsubstituted C6-C20 aryl group, a substituted or unsubstituted C6-C20 aryloxy group, a substituted or unsubstituted heteroaryl group, a substituted or unsubstituted C6-C20 arylthio group, a cyano group, a substituted or unsubstituted amino group, a substituted or unsubstituted aminocarboxy group, a C1-C10 alkylsulfonylamino group, a C6-C20 arylsulfonylamino group, a C2-C10 alkyl group having an N-substituted imino group at 1-position, a C7-C20 aralkyl group having an N-substituted imino group, an imido group, a C1-C20 aliphatic or aromatic acyl group, a carboxyl group, a C2-C20 alkoxycarbonyl group, a C6-C10 aryloxycarbonyl group, a substituted or unsubstituted aminosulfonyl group or a substituted or unsubstituted carbamoyl group, s represents an integer of 0 to (4-n), and herein, R8 or R9 may be bonded with the neighboring substituent to form a ring together with the carbon atom to which it is bonded.

* * * * *